(12) United States Patent
Sueki

(10) Patent No.: US 8,839,671 B2
(45) Date of Patent: Sep. 23, 2014

(54) MEASUREMENT METHOD AND MEASUREMENT DEVICE

(75) Inventor: Mitsuru Sueki, Shioya-gun (JP)

(73) Assignee: TS Tech Co., Ltd., Saitama-Ken (JP)

( * ) Notice: Subject to any disclaimer, the term of this patent is extended or adjusted under 35 U.S.C. 154(b) by 509 days.

(21) Appl. No.: 13/128,349

(22) PCT Filed: Dec. 9, 2009

(86) PCT No.: PCT/JP2009/070615
§ 371 (c)(1),
(2), (4) Date: Dec. 29, 2011

(87) PCT Pub. No.: WO2010/067826
PCT Pub. Date: Jun. 17, 2010

(65) Prior Publication Data
US 2012/0103100 A1    May 3, 2012

(30) Foreign Application Priority Data

Dec. 9, 2008    (JP) .................... 2008-313391

(51) Int. Cl.
*G01N 29/00* (2006.01)
*G01N 3/48* (2006.01)
*G01N 3/40* (2006.01)
*G01B 5/06* (2006.01)

(52) U.S. Cl.
CPC .......... *G01B 5/06* (2013.01); *G01N 2203/0682* (2013.01); *G01N 3/405* (2013.01); *G01N 2203/0005* (2013.01); *G01N 2203/0676* (2013.01); *G01N 3/40* (2013.01)
USPC .................................. 73/573; 73/81; 73/602

(58) Field of Classification Search
USPC ................ 73/579, 573, 602, 663, 574, 81, 83
See application file for complete search history.

(56) References Cited

U.S. PATENT DOCUMENTS

| | | | |
|---|---|---|---|
| 4,646,571 A * | 3/1987 | Kising et al. ................. | 73/573 |
| 5,092,175 A * | 3/1992 | Winckler et al. ............. | 73/573 |
| 5,216,921 A * | 6/1993 | Tsuboi ......................... | 73/579 |
| 5,438,872 A * | 8/1995 | Kobayashi et al. ........... | 73/597 |
| 5,766,137 A * | 6/1998 | Omata ......................... | 600/587 |
| 5,965,820 A * | 10/1999 | Ogawa ......................... | 73/663 |
| 6,539,781 B1 * | 4/2003 | Crezee ......................... | 73/81 |
| 6,854,331 B2 * | 2/2005 | Omata ......................... | 73/573 |
| 6,880,379 B2 * | 4/2005 | Hedberg et al. ............. | 73/12.01 |
| 7,565,841 B2 * | 7/2009 | Omata et al. ................. | 73/573 |
| 2009/0293619 A1 * | 12/2009 | Yoshinami et al. .......... | 73/588 |

FOREIGN PATENT DOCUMENTS

| | | |
|---|---|---|
| JP | 1189583 A | 7/1989 |
| JP | 5322730 A | 12/1993 |
| JP | 10288577 A | 10/1998 |
| JP | 2005188948 A | 7/2005 |
| JP | 2008145330 A | 6/2008 |
| JP | 200839789 A | 9/2009 |

* cited by examiner

Primary Examiner — Helen Kwok
(74) Attorney, Agent, or Firm — Browdy and Neimark, PLLC

(57) ABSTRACT

In the measurement method, a vibrator (5) of a detection unit (4) is relatively moved against a plate (3) of which surface is flat having predetermined area. The vibrator (5) which is vibrating is moved closer to a surface of an object-to-be-measured (1) which is mounted on the plate (3) until the frequency thereof is varied. A position where the frequency of the vibrator (5) is varied is output as a contact position where the vibrator (5) is contacted to the object-to-be-measured (1). Then, thickness of the object-to-be-measured (1) is measured by comparing the position where the vibrator (5) is contacted to the object-to-be-measured (1) with a surface position of the plate (3).

7 Claims, 8 Drawing Sheets

MEASUREMENT METHOD AND MEASUREMENT DEVICE

TECHNICAL FIELD

The present invention relates to a measurement method and a measurement device to measure thickness and hardness of cloth and leather material used for seats for vehicles and the like.

BACKGROUND ART

In the related art, it has been known a configuration to measure thickness of a disk owing to wavelength of reflection light as irradiating the disk with light (see Patent document 1). It has been also known a configuration to measure hardness owing to variation of a magnetic characteristic value of stainless steel as flowing current to the stainless steel (see Patent document 2). It has been also known a configuration to measure hardness of an object-to-be-measured (i.e., a measurement target) by utilizing frequency variation of a vibrator (see Patent document 3).

Patent document 1: JP 2008-39789A
Patent document 2: JP 2005-188948A
Patent document 3: JP 1-189583A

DISCLOSURE OF THE INVENTION

With the configuration to measure thickness owing to wavelength of reflection light among the above known technologies, there has been a problem that measurement accuracy cannot be ensured for cloth and leather material with which wavelength of reflection light is largely varied from part to part. In addition, there has been a problem of low operability because this configuration is for only thickness measurement and is incapable of measuring hardness.

With the configuration to measure hardness owing to variation of a magnetic characteristic value among the above known technologies, there has been a problem that measurement accuracy cannot be ensured for cloth and leather material with which the variation of the magnetic characteristics is small. In addition, there has been a problem of low operability because this configuration is for only thickness measurement and is incapable of measuring thickness.

With the configuration to measure hardness of an object-to-be-measured by utilizing frequency variation of a vibrator among the above known technologies, there has been a problem that delicate measurement is difficult to be performed as measurement of hardness not being easy only with the frequency variation at the time when the vibrator is contacted to the object-to-be-measured. In addition, there has been a problem of low operability because this configuration is for only thickness measurement and is incapable of measuring thickness.

In this application, it is devised to be capable of measuring thickness and hardness in one process even for a measurement target such as cloth and leather material.

According to the present invention, since a contact position is output owing to frequency variation of a vibrator 5, measurement of the contact position can be accurately performed. Further, thickness can be easily measured even for an object-to-be-measured 1 such as cloth and leather material.

Further, according to the present invention, since hardness is measured owing to pressure of reaction force against the vibrator 5 with movement of a predetermined distance from the contact position which is obtained through the frequency variation of the vibrator 5, measurement accuracy can be improved so as to measure hardness difference in the order of difference in texture with the object-to-be-measured 1 such as cloth and leather material. Here, hardness measurement can be performed in continuous operation subsequent to thickness measurement at the contact position, so that operability can be improved.

Further, according to the present invention, since measurement is performed while the object-to-be-measured 1 is held by a holder 35 from the upper side, it is possible to provide a device to easily measure thickness and hardness even for the object-to-be-measured 1 such as cloth and leather material.

BEST MODE FOR CARRYING OUT THE INVENTION

Embodiments of a device to perform a method of the present invention will be described with reference to the drawings. An object-to-be-measured 1 is a measurement target of a measurement device 2 for measuring thickness and hardness thereof (see FIG. 4). The object can be measured by the measurement device 2 as long as being shaped like a flat cloth having predetermined thickness, length and width.

The object-to-be-measured (i.e., the measurement target) 1 may be arbitrarily formed as long as being formed like a cloth such as being formed of leather or artificial leather and being formed in a multi-layered structure as sticking urethane and the like thereto. In particular, this application focuses on leather products which are used for vehicle interior such as seats and lining.

The measurement device 2 is configured to include a flat plate 3 on which the object-to-be-measured 1 is placed and a detection unit 4 which is moved relatively against the plate 3. The plate 3 is adoptable as long as the surface thereof is flat and smooth having predetermined area with predetermined hardness to be capable of supporting the object-to-be-measured 1. In the present embodiment, the plate 3 is formed of glass material. However, it is also possible to be formed of other hard material such as quartz.

Figure 4:
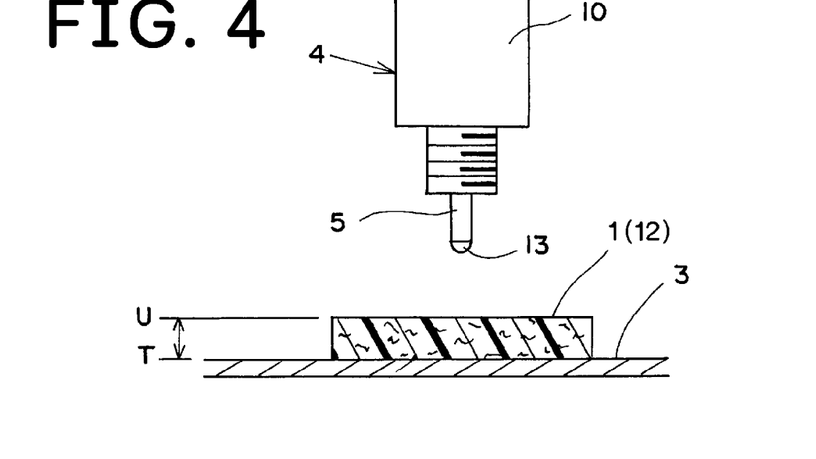
FIG. 4 is a sectional view in a state that an object-to-be-measured is mounted on the plate.

The object-to-be-measured 1 is mounted on the surface of the plate 3 (see FIG. 4). Next, a vibrating vibrator 5 of the detection unit 4 is moved closer to a surface of the object-to-be measured 1 (see FIG. 5). The vibrator 5 is to be moved closer until the frequency of the vibrator 5 is varied, and then, the position where the frequency of the vibrator 5 is varied is output to a control unit 6 as a contact position where the vibrator 5 is contacted to the object-to-be-measured 1. The control unit 6 measures thickness of the object-to-be-measured 1 by comparing the position where the object-to-be-measured 1 contacts the vibrator 5 with the surface position of the plate 3.

Figure 6:
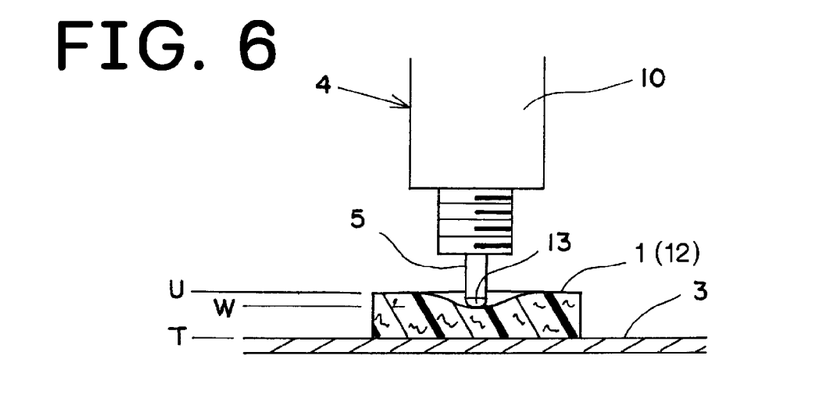
FIG. 6 is a sectional view in a state that the vibrator is measuring hardness of the object-to-be-measured.

After the measurement signal of the thickness of the object-to-be-measured 1 is transmitted to the control unit 6, the vibrator 5 is further moved by a predetermined distance toward the plate 3 from the contact position of the surface of the object-to-be-measured 1 (see FIG. 6). Accordingly, since the vibrator 5 presses the object-to-be-measured 1, contact pressure between the vibrator 5 and the object-to-be-measured 1 is varied as a result of reaction force due to material of the object-to-be-measured 1 against the vibrator 5. The pressure variation is detected and output to the control unit 6. The hardness of the object-to-be-measured 1 is measured by the control unit 6 as processing comparison between the reaction force pressure from the object-to-be-measured 1 and previously-obtained hardness information.

Figure 3:
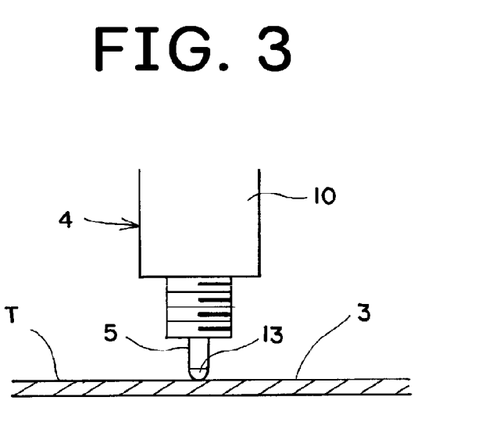
FIG. 3 is a sectional view in a state that the vibrator is contacted to the plate.

Here, the vibrating vibrator 5 is moved closer to the surface of the plate 3 on which nothing is placed until the frequency is varied, and then, the distal end position of the vibrator 5 is output to the control unit 6 as the surface position of the plate 3 when the frequency of the vibrator 5 is varied (see FIG. 3). Accordingly, since the surface position of the plate 3 is accurately detected, measurement accuracy is improved for comparing the position where the vibrator 5 contacts the object-to-be-measured 1 with the surface position of the plate 3.

The plate 3 is installed in an arbitrary orientation as long as the plate 3 and the detection unit 4 are to be contacted as being relatively moved to each other. For easier understanding, following description is provided as the plate 3 is installed approximately horizontal and the detection unit 4 is vertically moved against the plate 3. The vibrator 5 which is vertically movable is arranged at the detection unit 4 in a case 10. The vibrator 5 is configured to be vertically moved against the case 10 as slightly vibrating owing to an excitation unit 11 with ultrasonic waves and the like.

In a state that nothing is placed on an upper face (i.e., the surface) of the plate 3 (see FIG. 2), the distal end of the vibrator 5 is contacted to the upper face of the plate 3 (see FIG. 3) when the vibrator 5 is lowered. Accordingly, the frequency variation of the vibrator 5 occurs between before-contacting and after-contacting to the upper face of the plate 3. A signal of the height position of the vibrator 5 when the frequency of the vibrator 5 is varied is transmitted to the control unit 6 as a before-measurement zero position T as zero thickness (see FIG. 3). The control unit 6 memorizes the before-measurement thickness zero position T and initialization is completed.

The object-to-be-measured 1 is mounted on the plate 3 after raising the vibrator 5 (see FIG. 4). Then, the vibrator 5 is lowered once again. When the distal end of the vibrator 5 is contacted to an upper face (i.e., the surface) of the object-to-be-measured 1, the frequency of the vibrator 5 is varied. A signal at the time when the vibration variation occurs is transmitted to the control unit 6 as an object-to-be-measured thickness position U (see FIG. 5). The thickness of the object-to-be-measured 1 is measured by the control unit 6 as processing comparison between the before-measurement thickness zero position T and the object-to-be-measured thickness position U.

When the vibrator 5 is further lowered by a predetermined distance W from the object-to-be-measured thickness position U where the vibrator 5 is contacted to the upper face of the object-to-be-moved 1 (FIG. 6), lowering pressure of the vibrator 5 is varied as a result of reaction force exerted from the object-to-be-measured 1 to the lowering of the vibrator 5. A signal of a value of the lowering pressure variation is transmitted to the control unit 6. The control unit 6 measures the hardness of the object-to-be-measured 1 based on the lowering pressure variation value.

That is, the contacting is sensed by the frequency variation of the vibrator 5, and then, the thickness of the object-to-be-measured 1 is measured owing to the distance from the upper face of the plate 3 to the contact position simultaneously when the existence of the object-to-be-measured 1 is sensed. Then, the hardness (i.e., degree of hardness) of the object-to-be-measured 1 is measured by measuring variation of the lowering pressure of the vibrator 5 as further lowering the vibrator 5 slightly by the predetermined distance W.

Then, when the above operation is repeated as placing another object-to-be-measured 1 on the plate 3, measurement of thickness and hardness of the object-to-be-measured 1 can be performed. Here, a reference body 12 formed of material such as silicone having predetermined elasticity is placed on the plate 3 (see FIG. 4) and the vibrator 5 is lowered. When the distal end of the vibrator 5 is contacted to an upper face of the reference body 12, frequency variation of the vibrator 5 occurs. A signal at the time when the vibration variation occurs is transmitted to the control unit 6 as the "contacting" of the vibrator 5. The control unit 6 sets the signal value as a reference value of the "contacting" of the vibrator 5.

When the vibrator 5 is further lowered by the predetermined distance W from the contact position where the vibrator 5 is contacted to the upper face of the reference body 12 (see FIG. 6), lowering pressure of the vibrator 5 is varied as a result of reaction force exerted from the reference body 12 to the lowering of the vibrator 5. A value of the lowering pressure variation indicating the hardness of the reference body 12 is transmitted to the control unit 6. The control unit 6 performs setting or correction processing of the reaction force pressure value of the vibrator 5 by comparing the lower pressure variation value and the previously-obtained hardness information when the vibrator 5 presses the reference body 12 which has the predetermined hardness.

Accordingly, when the distal end of the vibrator 5 is contacted to the upper face of the plate 3 and variation of a degree to the reference value of the "contacting" occurs at the frequency of the vibrator 5 as lowering the vibrator 5, a signal of a height position of the vibrator 5 is transmitted to the control unit 6 as the before-measurement thickness zero position T and initialization is completed.

Further, when the variation of a degree to the reference value of the "contacting" occurs at the frequency of the vibrator 5 while the distal end of the vibrator 5 is contacted to the upper face of the object-to-be-measured 1, a signal of the object-to-be-measured thickness position U is transmitted to the control unit 6. The control unit 6 measures the thickness of the object-to-be-measured 1 by comparing the thickness zero position before-measurement thickness zero position T and the object-to-be-measured thickness position U.

As the vibrator 5 is further lowered by the predetermined distance W from the object-to-be-measured thickness position U where the vibrator 5 is contacted to the upper face of the object-to-be-measured 1, reaction force is exerted from the object-to-be-measured 1. The control unit 6 measures the hardness of the object-to-be-measured 1 by comparing the variation of the lowering pressure of the vibrator 5 against lowering of the predetermined distance with the lowering pressure variation value being reference of the reference body 12.

Figure 7:
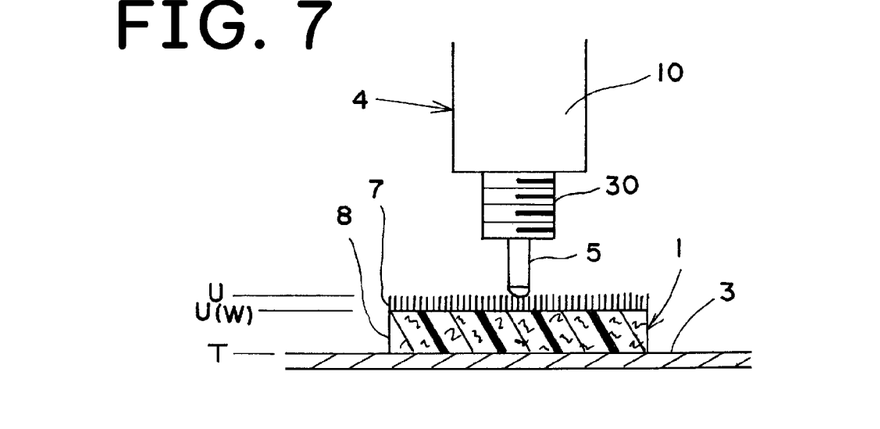
FIG. 7 is a sectional view in a state that the vibrator is contacted to a raised fabric portion of the object-to-be-measured.
Figure 8:
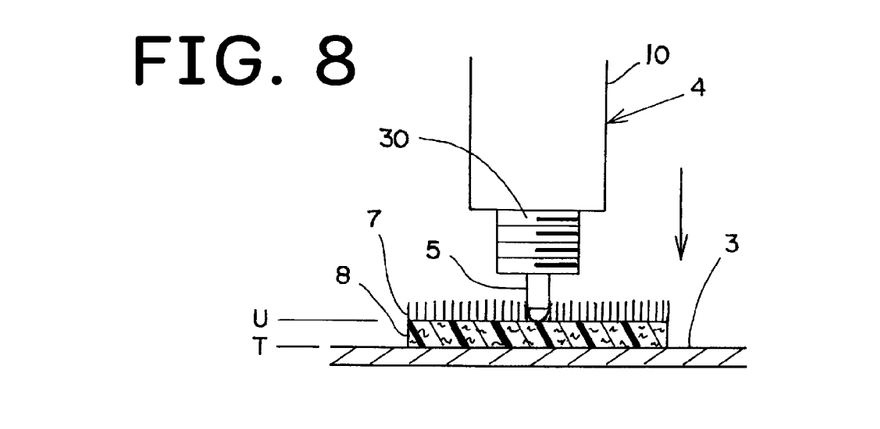
FIG. 8 is a sectional view in a state that the vibrator is contacted to a main body portion of the object-to-be-measured.
Figure 9:
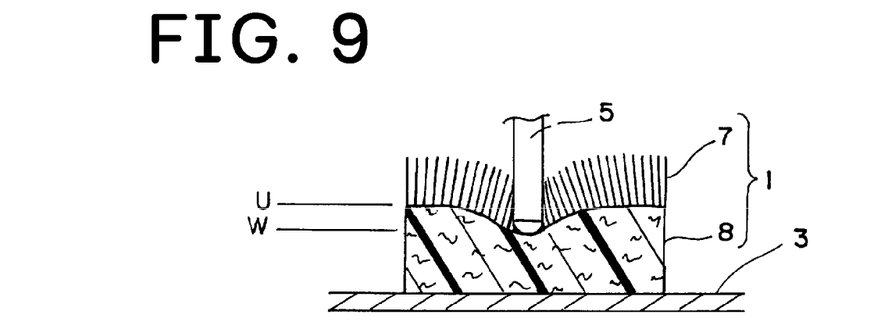
FIG. 9 is a sectional view in a state that the vibrator is measuring hardness as pressing the main body portion of the object-to-be-measured.
Figure 10:
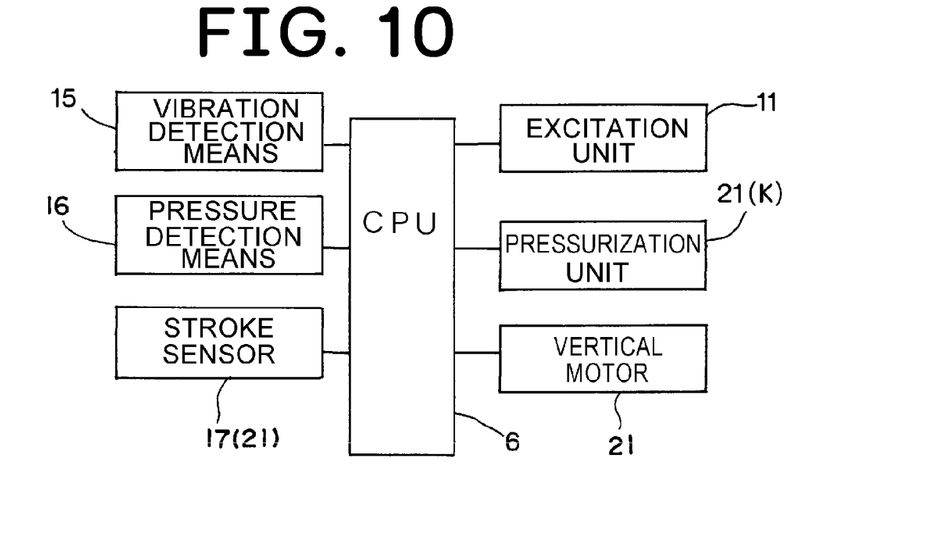
FIG. 10 is a block diagram.

As illustrated in FIGS. 7 and 8, when raised fabric 7 exists as a surface of a main body 8 of the object-to-be-measured 1 such as back skin is raised, for example, various conditions are changed including a vertical movement amount of the vibrator 5, lowering pressure of the vibrator 5, lowering speed of the vibrator 5, and press depth of the object-to-be-measured 1 due to the vibrator 5. Here, frequency variation of the vibrator 5 at the time when the vibrator 5 is contacted to the portion of the raised fabric 7 is not processed as the contacting. Instead, it is configured that frequency variation of the vibrator 5 at the time when the vibrator 5 is contacted to a portion of the main body 8 of the object-to-be-measured 1 while further lowering the vibrator 5 from a distal end of the raised fabric 7 is processed as the contacting. The above configuration is preferable as the measurement accuracy being improved.

Naturally, there is difference between the frequency when the vibrator 5 is contacted to the portion of the raised fabric 7 and the frequency when the vibrator 5 is contacted to the portion of the main body 8 of the object-to-be-measured 1 as a result of difference of characteristics thereof. Accordingly, when the control unit 6 performs a discrimination process between the contacting to the portion of the raised fabric 7 and the contacting to the portion of the main body 8 based on the frequency variation of the vibrator 5, the detection unit 4 can measure thickness of the portion of the raised fabric 7 and the portion of the main body 8 respectively.

It is possible to measure the thickness and hardness of the portion of the raised fabric 7 by detecting contact resistance due to lowering of the predetermined distance W until the surface of the portion of the main body 8 as perceiving the position of contacting to the portion of the raised fabric 7 in FIG. 7 as the object-to-be-measured thickness position U, for example. As illustrated in FIG. 8, it is possible to measure the thickness and hardness of the portion of the main body 8 by detecting contact resistance due to further lowering of the predetermined distance W as perceiving the contacting position to the surface of the main body 8 portion as the object-to-be-measured thickness position U after performing the discrimination process between the contacting to the portion of the raised fabric 7 and the contacting to the portion of the main body 8.

Accordingly, it becomes possible to measure the thickness and hardness of objects-to-be-measured 1 having various characteristics. In particular, it is possible to measure hardness difference in the order of difference in texture with the object-to-be-measured 1 such as cloth and leather material. Therefore, measurement accuracy is improved and quality determination accuracy of the objects-to-be-measured 1 is improved, so that quality control can be easily performed.

The detection unit 4 may be arbitrarily configured as long as including the excitation unit 11 to apply vibration to the vibrator 5 with a distal contact 13 arranged at the lower end of the vibrator 5, vertically moving means 14 to vertically move the vibrator 5, vibration detection means 15 to detect frequency of the vibrator 5 and variation thereof, pressure detection means 16 to detect lowering pressure (i.e., contact pressure) of the vibrator 5 and variation thereof, a stroke sensor 17 to detect a vertical amount of the vibrator 5, and the control unit 6 to control the above.

As an example of the above, the vibrator 5 which is vertically movable is arranged in the case 10 and the excitation unit 11 is arranged to the vibrator 5. The excitation unit 11 is constituted with a so-called ultrasonic transmitter and the like (not illustrated), for example. In the present embodiment, the vibrator 5 and the excitation unit 11 are integrally arranged (see FIG. 11). The vibration detection means 15 is arranged between the vibrator 5 and the excitation unit 11. The vibration detection means 15 is constituted with a tactile sensor which is also called a touch sensor and the like, for example. The vibration detection means 15 of the present embodiment is configured to detect vibration pressure as well as the frequency so as to improve sense accuracy.

Figure 11:
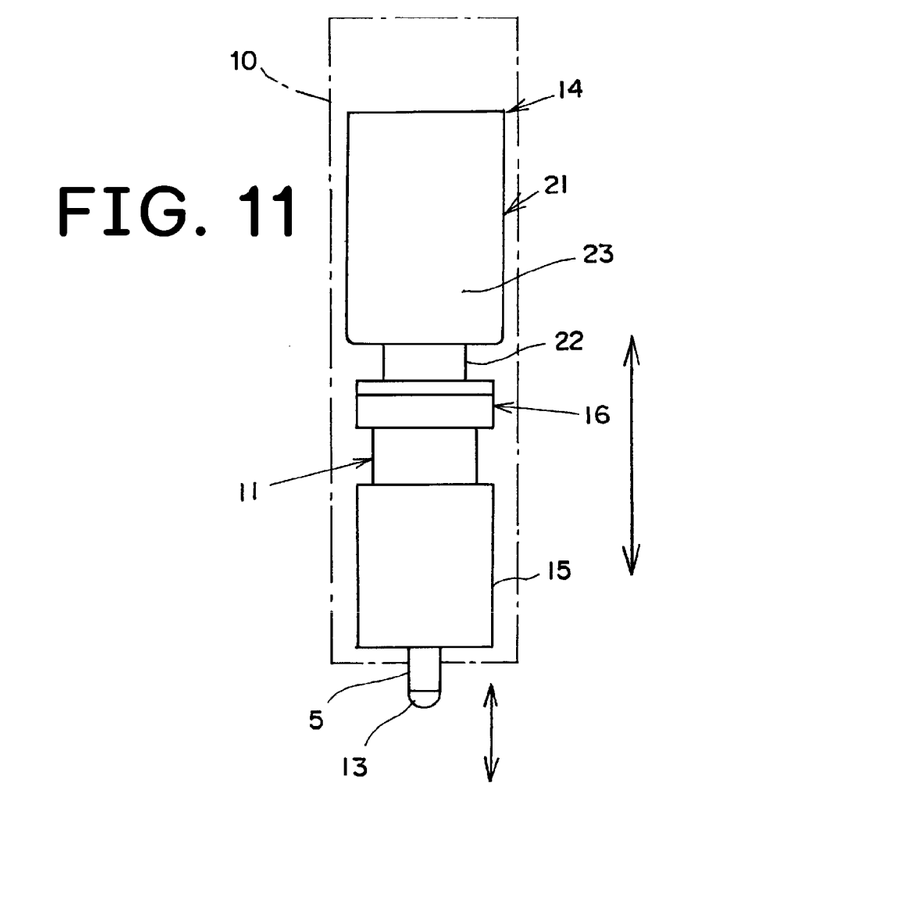
FIG. 11 is a front view illustrating an example of the detection unit.

The vertically moving means 14 is configured to elongate and contract an output shaft 22 of a vertically movable motor 21 from a motor main body 23 and the pressure detection means 16 is attached to a distal end of the output shaft 22 (see FIG. 11).

In the present embodiment, the vertically movable motor 21 also functions as pressurization means to press the vibrator 5 to the object-to-be-measured 1. However, it is also possible to arrange pressurization means K to press the vibrator 5 to the object-to-be-measured 1 separately from the vertically movable motor 21.

In the present embodiment, the vertically movable motor 21 is constituted with a so-called step motor. Since the vertical amount of the vibrator 5 can be set by the rotational amount of the vertically movable motor 21, the vertically movable motor 21 also functions as the stroke sensor 17 to detect the vertical amount of the vibrator 5. The excitation unit 11 is attached below the pressure detection means 16 (see FIG. 11).

A mechanism to vertically move the vibrator 5 with the vertically movable motor 21 may be arbitrarily configured. The vertically movable motor 21 may be configured that the output shaft 22 thereof is rotatable in a forward-reverse manner and an output gear (not illustrated) of the output shaft 22 is engaged with a rack (not illustrated) arranged at the vibrator 5 side.

Figure 1:
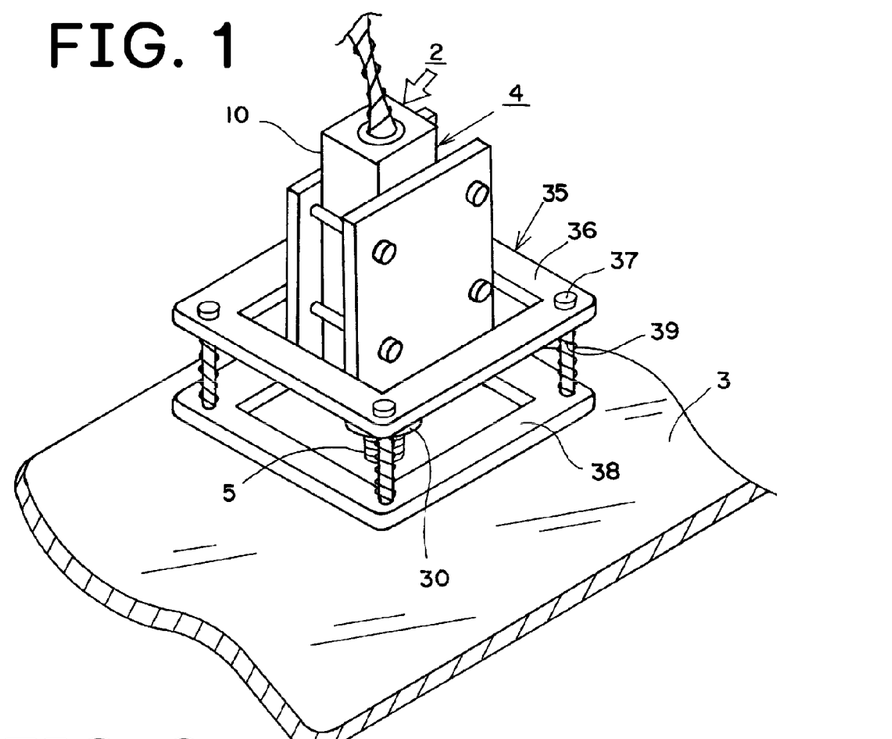
FIG. 1 is a perspective view of a detection unit of a measurement device and a part of a plate.
Figure 2:
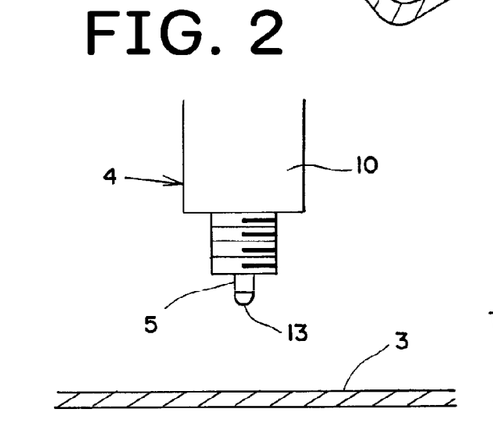
FIG. 2 is a sectional view of a vibrator and the plate before measurement.
Figure 12:
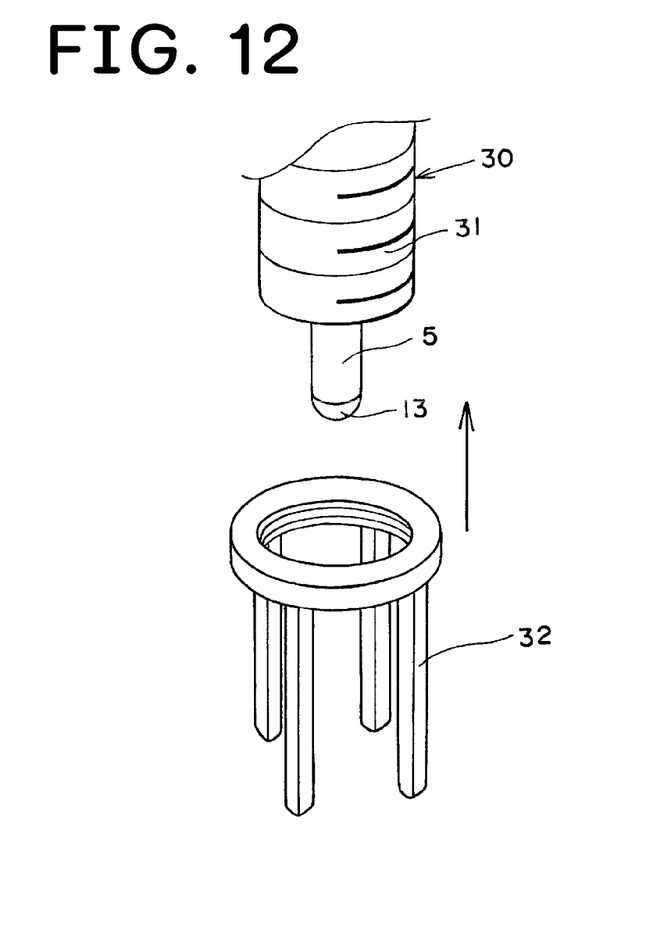
FIG. 12 is a perspective view in a state that a sensor protection cover is to be attached to a sensor protection cylinder.

A sensor protection cylinder 30 is arranged at the lower part of the case 10 (see FIGS. 1 and 2). A thread groove 31 is formed at the outer circumferential face of the sensor protection cylinder 30. A sensor protection cover 32 is screwed with the thread groove 31 to be vertically movable against the sensor protection cylinder 30 (see FIG. 12).

Figure 13:
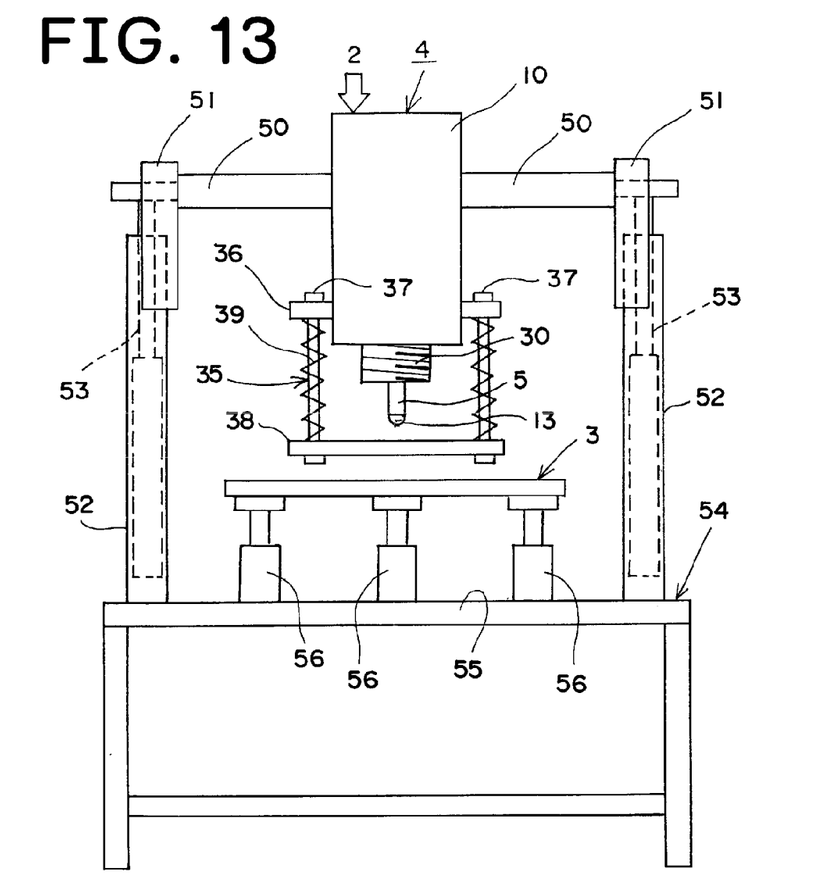
FIG. 13 is a front view of the measurement device.
Figure 14:
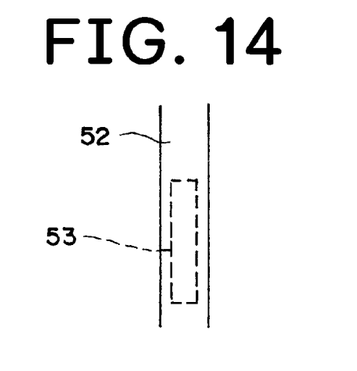
FIG. 14 is an enlarged view of a pole and a push cylinder.

A holder 35 to hold the object-to-be-measured 1 from the upper side is arranged around the sensor protection cylinder 30 (see FIG. 1). In the holder 35, a rectangle-shaped upper frame 36 is fixed to the case 10 side and vertical shafts 37 are arranged at the four corners of the upper frame 36. A lower frame 38 is attached to the vertical shafts 37 as being vertically movable and a spring 39 is arranged at the outer circumference of each vertical shaft 37 to urge the lower frame 38 to be continuously lowered against the upper frame 36 (see FIG. 13).

Here, the lower end of the vibrator 5 is located between the upper face of the lower frame 38 and the lower end of the sensor protection cylinder 30, at first. When the case 10 is lowered, the lower frame 38 is lowered together. Then, when the lower frame 38 is contacted to the object-to-be-measured 1, the lower frame 38 is moved upward and the object-to-be-measured 1 is held with elastic force of the spring 39. The lowering of the case 10 is stopped in this state, and then, only the vibrator 5 is lowered against the case 10 to be contacted to the upper face of the object-to-be-measured 1. Further, only the vibrator 5 is lowered by the predetermined distance W so as to measure hardness of the object-to-be-measured 1 as pressing the object-to-be-measured 1.

In a state that the vibrator 5 is accommodated in the case 10, the sensor protection cover 32 is located below the lower end of the vibrator 5 so as to prevent the lower end of the vibrator 5 from being unintentionally contacted to the plate 3.

The case 10 is attached to a lateral rod 50 extending in the lateral direction (i.e., the horizontal direction). A pair of guide bodies 51 is attached to both ends of the lateral rod 50 (see FIG. 13) and is attached to a pair of poles 52 as being vertically movable. A push cylinder 53 to vertically move the lateral rod 50 is arranged at the pole 52. The lower part of the pole 52 is fixed to an upper plate 55 of a body frame 54.

The case 10 is attached to the lateral rod 50 extending in the lateral direction (i.e., the horizontal direction). The pair of guide bodies 51 is attached to both ends of the lateral rod 50 and is attached to a pair of poles 52 as being vertically movable. The push cylinder 53 to vertically move the guide body 51 or the lateral rod 50 is arranged at the pole 52. The lower part of the pole 52 is fixed to the upper plate 55 of the body frame 54.

The plate 3 located between the bilateral poles 52 is arranged on the upper plate 55 via plate vertical-support units 56. The plate 3 is arranged by the plate vertical-support units 56 so that any part of the whole upper face intersects with the vibrator 5 at a right angle (vertically). Accordingly, measurement accuracy of the detection unit 4 is improved.

Figure 18:
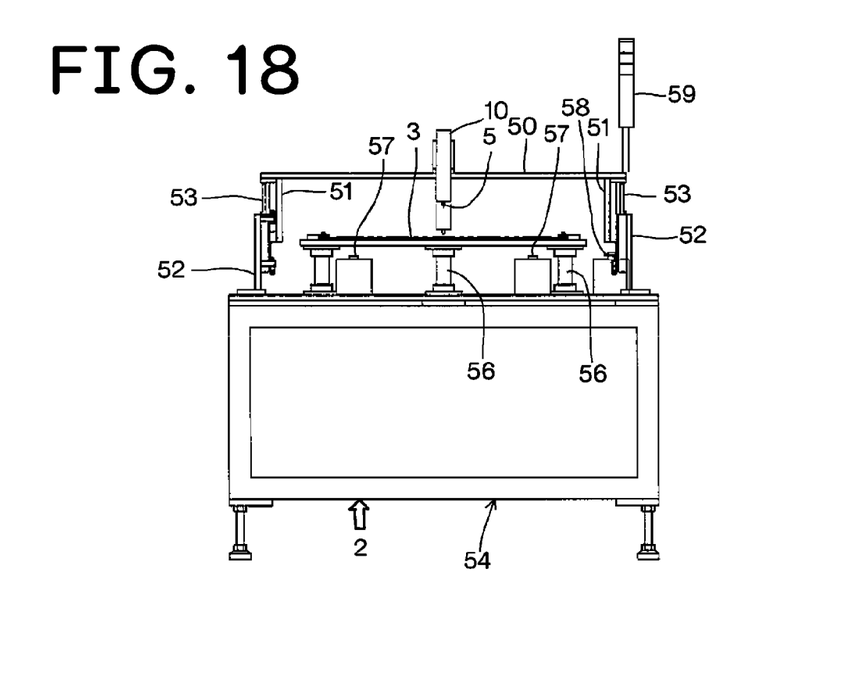
FIG. 18 is a front view of another embodiment of a measurement device.
Figure 19:
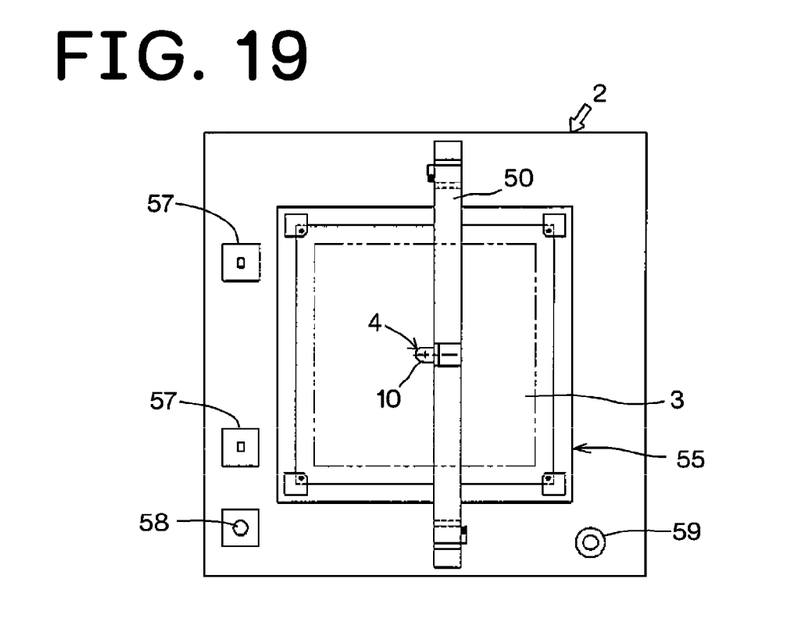
FIG. 19 is a plane view of the other embodiment of the measurement device.
Figure 20:
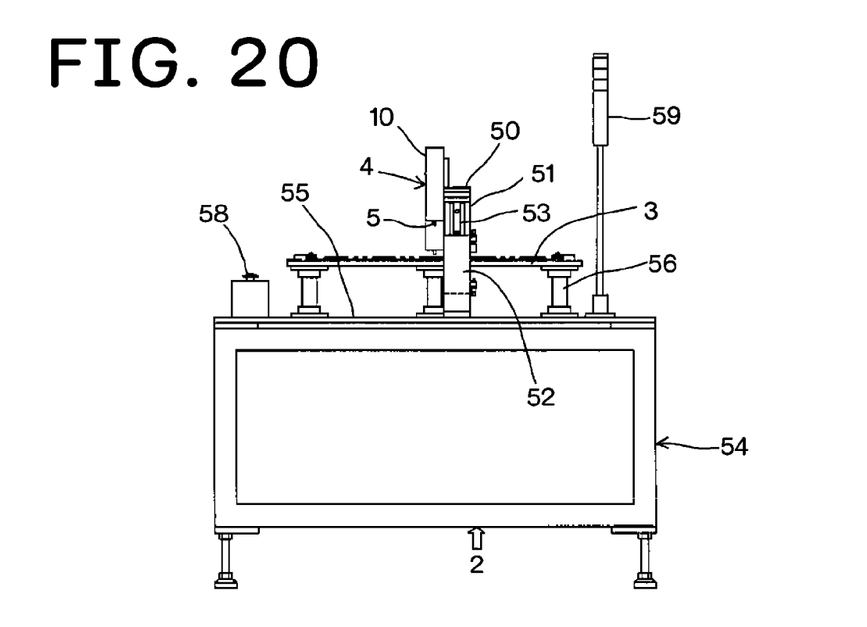
FIG. 20 is a side view of the other embodiment of the measurement device.

A matched pair of operation switches 57 is illustrated in FIG. 18. It is preferable to start measurement when both of the operation switches 57 are operated, so that operational safety is improved.

An emergency stop switch 58 and determination result notification means 59 for the object-to-be-measured 1 are illustrated in FIG. 18. In the present embodiment, the determination result notification means 59 is constituted with vertically-aligned three lamps. Lighting of the upper lamp notifies quality acceptance of the object-to-be-measured 1, lighting of the middle lamp notifies unsuitable thickness, and lighting of the lower lamp notifies unsuitable hardness.

When a plurality of the detection units 4 are arranged in parallel in a left-right direction or a front-rear direction, measurement can be concurrently performed at a plural part of the object-to-be-measured 1 so as to improve operability of measurement operation. For example, the plural detection units 4 are arranged in parallel in the longitudinal direction of the lateral rod 50. Since it is only required to mutually contact the object-to-be-measured 1 on the plate 3 and the detection unit 4, the case 10 may be lowered along with the lateral rod 50 by the push cylinder 53 and the vibrator 5 may be lowered by the vertically movable motor 21 from a predetermined height.

(Operation of Embodiment)

When the vibrator 5 is lowered without placing the object-to-be-measured 1 on the plate 3 (see FIG. 2), the distal end of the vibrator 5 is contacted to the upper face of the plate 3 (see FIG. 3). Accordingly, the frequency variation of the vibrator 5 occurs between before-contacting and after-contacting to the upper face of the plate 3. The signal that the height position of the vibrator 5 when the frequency of the vibrator 5 is varied is transmitted to the control unit 6 as the before-measurement thickness zero position T as zero thickness. The control unit 6 memorizes the before-measurement thickness zero position T and initialization is completed.

Next, the vibrator 5 is raised once and the object-to-be-measured 1 is placed on the plate 3 (see FIG. 4). When the vibrator 5 is lowered again, the distal end of the vibrator 5 is contacted to the upper face of the object-to-be-measured 1 (see FIG. 5). When the distal end of the vibrator 5 is contacted to an upper face of the object-to-be-measured 1, the frequency of the vibrator 5 is varied. A signal of the height position at the time when the vibration variation of the vibrator 5 occurs is transmitted to the control unit 6 as an object-to-be-measured thickness position U (see FIG. 5).

The thickness of the object-to-be-measured 1 is measured by the control unit 6 as performing comparison between the before-measurement thickness zero position T and the object-to-be-measured thickness position U. When the vibrator 5 is further lowered by the predetermined distance W from the object-to-be-measured thickness position U where the vibrator 5 is contacted to the upper face of the object-to-be-measured 1, the lowering pressure (i.e., the contact pressure) of the vibrator 5 is varied as a result of reaction force exerted from the object-to-be-measured 1 to the lowering of the vibrator 5.

Then, a signal of a varied value of the lowing pressure variation is transmitted to the control unit 6. The control unit 6 measures the hardness of the object-to-be-measured 1 with calculation based on the lowering pressure variation value. That is, the contacting between the vibrator 5 and the object-to-be-measured 1 is sensed based on the frequency variation of the vibrator 5, and then, the thickness of the object-to-be-measured 1 is measured based on the distance from the upper face of the plate 3 to the contact position between the vibrator 5 and the object-to-be-measured 1 simultaneously when the existence of the object-to-be-measured 1 is sensed.

Continuously, the hardness of the object-to-be-measured 1 (i.e., the degree of hardness) is measured by measuring variation of the lowering pressure of the vibrator 5 as further lowering the vibrator 5 slightly by the predetermined distance W (see FIG. 6). Since the control unit 6 can be set to automatically memorize the information of the thickness and hardness of the object-to-be-measured 1, obtaining operation of the information of the thickness and hardness of the object-to-be-measured 1 can be automated.

Here, in the case that the contacting is determined by comparing the vibration variation when the vibrator 5 is contacted to the upper face of the object-to-be-measured 1 with previously-assumed contact information or contact information obtained through accumulation of measurement results, measurement accuracy of the height position is improved. Similarly, in the case that the hardness is determined as well by comparing the variation of the lowering pressure (i.e., the contact pressure) when the vibrator 5 is lowered by the predetermined distance W with previously-assumed hardness information or hardness information obtained through accumulation of measurement results, measurement accuracy of the hardness is improved.

In this case, the hardness is measured based on the variation of contact pressure caused by lowing of the vibrator 5. Accordingly, the measurement is performed easily and accurately compared to the case of calculating the hardness based on the vibration variation. Further, since the thickness and hardness can be measured while lowering the vibrator 5, measurement operation for the thickness and hardness can be easily performed in a continued manner with a reasonable structure. Accordingly, workability and operability can be improved and overall operation for quality control can be rationalized.

In the case that information of the thickness and hardness is previously set at the control unit 6 in accordance with the object-to-be-measured 1 for measurement, quality determination operation of the thickness and hardness can be automated for assumed specifications of the object-to-be-measured 1, so that operational efficiency can be improved.

In the case that the control unit 6 is provided with setting of various conditions such as a vertical movement amount of the vibrator 5, lowering pressure of the vibrator 5, lowering speed of the vibrator 5, and press depth of the object-to-be-measured 1 due to the vibrator 5 in accordance with the object-to-be-measured 1 to be a measurement target, it is possible to measure various thickness and hardness of the object-to-be-measured 1.

Here, it is assumed that the reference body 12 formed of material such as silicone having predetermined elasticity is separately arranged, the reference body 12 is placed on the plate 3, the vibrator 5 is lowered to lower the distal end of the vibrator 5 until variation occurs at the frequency of the vibrator 5, and the signal of the vibration variation is transmitted to the control unit 6. In this case, the control unit 6 can set the signal value as the reference value of the frequency variation at the time when the vibrator 5 is "contacted" to the object-to-be-measured 1. Accordingly, it becomes easy to perform setting and measurement accuracy is improved.

Similarly, since reaction force is previously assumed from the reference body 12, the lowering pressure (i.e., the contact pressure) of the vibrator 5 is varied when the vibrator 5 is further lowered by the predetermined distance W from the contact S position where the vibrator 5 is contacted to the upper face of the reference body 12. The signal of the lowering pressure variation value against the lowering pressure of the vibrator 5 before being varied is transmitted to the control unit 6. The control unit 6 performs setting or correcting as a reference of "hardness determination" by comparing the pressure signal value with the previously-prepared hardness information of the reference body 12.

Accordingly, as the vibrator 5 is further lowered by the predetermined distance W from the object-to-be-measured thickness position U where the vibrator 5 is contacted to the upper face of the object-to-be-measured 1, reaction force is exerted from the object-to-be-measured 1. The control unit 6 measures the hardness of the object-to-be-measured 1 by comparing the variation value of the lowering pressure of the vibrator 5 against lowering of the predetermined distance with the hardness information of the reference body 12.

As a specific example, the control unit 6 is provided with setting of various conditions such as a vertical movement amount of the vibrator 5, lowering pressure of the vibrator 5, lowering speed of the vibrator 5, and press depth of the object-to-be-measured 1 due to the vibrator 5 in accordance with the object-to-be-measured 1 to be a measurement target.

Next, it is assumed that the reference body 12 formed of material such as silicone having predetermined elasticity is separately arranged, the reference body 12 is placed on the plate 3, the vibrator 5 is lowered to lower the distal end of the vibrator 5 until variation occurs at the frequency of the vibrator 5, and the signal of the vibration variation is transmitted to the control unit 6. In this case, the control unit 6 automatically performs setting or correcting with the signal value as the reference value for determination reference of the frequency variation at the time when the vibrator 5 is "contacted" to the object-to-be-measured 1.

Similarly, the control unit 6 performs setting or correcting of the reference value for "hard-soft determination" by comparing the variation of the lowering pressure of the vibrator 5 when the vibrator 5 is further lowered by the predetermined distance W from the contact S position where the vibrator 5 is contacted to the upper face of the reference body 12 with the assumed value of the reference body 12 which is previously assumed.

In this state, when the vibrator 5 is lowered without placing the object-to-be-measured 1 on the plate 3, the distal contact 13 of the vibrator 5 is contacted to the upper face of the plate 3. Accordingly, the vibration detection means 15 detects the frequency variation of the vibrator 5 between before-contacting and after-contacting with the upper face of the plate 3. The signal that the height position of the vibrator 5 when the frequency of the vibrator 5 is varied is transmitted to the control unit 6 as the before-measurement thickness zero position T as zero thickness. The control unit 6 memorizes the before-measurement thickness zero position T and initialization is completed.

Next, the vibrator 5 is raised once and the object-to-be-measured 1 is placed on the plate 3. The vibrator 5 is lowered again, and then, the vibration detection means 15 detects the frequency variation of the vibrator 5 caused by contacting of the distal end of the vibrator 5 to the upper face of the object-to-be-measured 1. A signal of the height position where the vibration variation signal occurs is transmitted from the vibration detection means 15 to the control unit 6 as the object-to-be-measured thickness position U. The control unit 6 measures the thickness of the object-to-be-measured 1 by performing comparison between the before-measurement thickness zero position T and the object-to-be-measured thickness position U.

Next, when the vibrator 5 is further lowered to previously-set height by the predetermined distance W from the object-to-be-measured thickness position U where the vibrator 5 is contacted to the upper face of the object-to-be-measured 1, the stroke sensor 17 detects that the vibrator 5 has arrived at the height for hardness measurement and lowing of the vibrator 5 is stopped. Then, the pressure detection means 16 detects the lowering pressure of the vibrator 5 due to reaction force exerted from the object-to-be-measured 1. The hardness of the object-to-be-measured 1 is measured through calculation by comparing the lowering pressure value of the vibrator 5 from the pressure detection means 16 with the lowering pressure variation value being the reference of hardness determination.

In this manner, the contacting between the vibrator 5 and the object-to-be-measured 1 is sensed based on the frequency variation of the vibrator 5, and then, the thickness of the object-to-be-measured 1 is measured based on the distance from the upper face of the plate 3 to the contact position between the vibrator 5 and the object-to-be-measured 1 simultaneously when the existence of the object-to-be-measured 1 is sensed. Continuously, the hardness of the object-to-be-measured 1 (i.e., the degree of hardness) is measured by measuring variation of the lowering pressure of the vibrator 5 as further lowering the vibrator 5 slightly by the predetermined distance W. Accordingly, the thickness and hardness of the object-to-be-measured 1 are measured in one process.

Since the measurement value is stored in the control unit 6, quality determination of the object-to-be-measured 1 can be instantaneously performed by comparing with the previously-set reference value of the thickness and hardness of the object-to-be-measured 1. As being performed by the detection unit 4, the quality determination of the object-to-be-measured 1 can be performed more accurately without requiring determination proficiency for an operator compared to quality determination performed manually by an operator. In addition, since the object-to-be-measured 1 is only required to be placed on the plate 3, it is possible to perform the measurement with a nondestructive method.

Further, since the measurement can be performed by placing the object-to-be-measured 1 onto the plate 3 and vertically moving the vibrator 5, operation can be continuously performed. Accordingly, operational efficiency of quality determination operation for the object-to-be-measured 1 can be improved and operational efficiency of overall quality control can be improved.

The mechanism to lower the vibrator 5 may be arbitrarily configured. Here, the case 10 is attached to the lateral rod 50 (see FIG. 13). A pair of the guide bodies 51 is attached to both ends of the lateral rod 50 and is attached to a pair of the poles 52 as being vertically movable. The push cylinder 53 to vertically move the lateral rod 50 is arranged at the pole 52. Accordingly, the lateral rod 50 is lowered by the push cylinder 53 and the entire case 10 is lowered as a result of lowering of the lateral rod 50.

Figure 15:
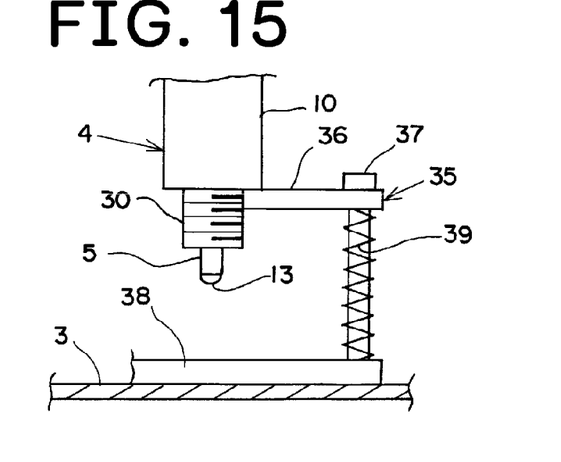
FIG. 15 is a sectional view in a state that a holder is contacted to the plate.
Figure 16:
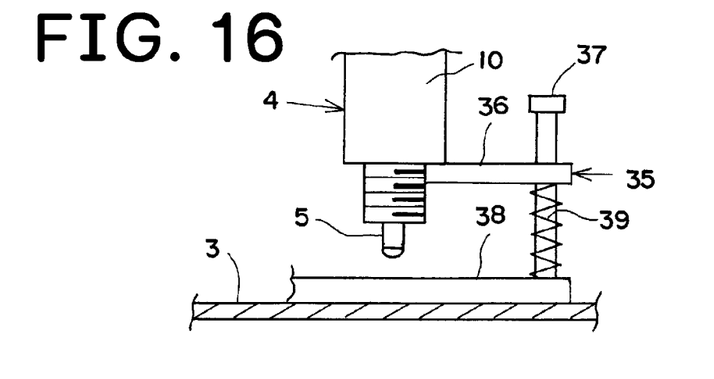
FIG. 16 is a sectional view in a state that a lower frame of the holder is moved upward.

The holder 35 to hold the object-to-be-measured 1 from the upper side is arranged around the vibrator 5 exposed as projecting downward from a lower part of the case 10. In the holder 35, the rectangle-shaped upper frame 36 is fixed to the case 10 side and the lower frame 38 is attached to the upper frame 36 with the vertical shafts 37 as being vertically movable. The spring 39 is arranged at the outer circumference of each vertical shaft 37 to urge the lower frame 38 to be always lowered against the upper frame 36. When the case 10 is lowered to the previously-set height by the push cylinder 53, the lower frame 38 is elastically contacted to the upper face of the object-to-be-measured 1 on the plate 3 (see FIG. 15). When the case 10 is further lowered, the lower frame 38 is moved upward against the upper frame 36 being opposed to the elastic force of the spring 39 as maintaining contacting to the upper face of the object-to-be-measured 1 (see FIG. 16).

Figure 17:
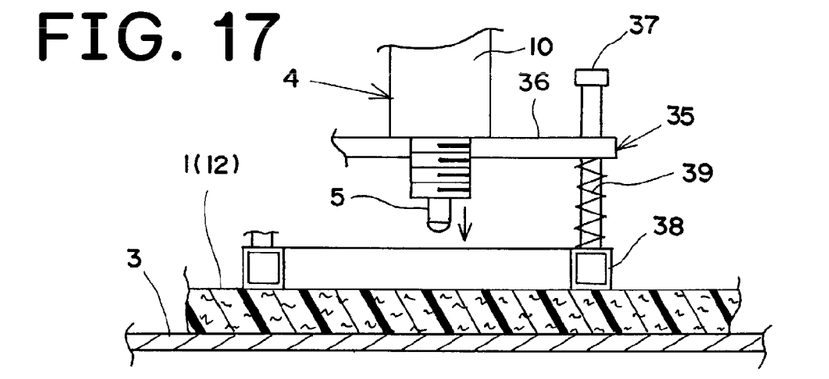
FIG. 17 is a sectional view in a state that the holder before contacting of the vibrator is contacted to the object-to-be-measured.

Then, when the holder 35 holds the object-to-be-measured 1 with the lower frame 38 at the vicinity where the vibrator 5 is contacted as the lower frame 38 being contacted to the upper face of the object-to-be-measured 1, the lowering of the case 10 is stopped (see FIG. 17).

Here, the lower end of the vibrator 5 is located between the lower frame 38 and lower end of the sensor protection cylinder 30, at first. The vibrator 5 of the case 10 and the lower frame 38 are lowered together, and then, the lower frame 38 is contacted forward to the object-to-be-measured 1. The lower frame 38 firmly holds the object-to-be-measured 1 with the elastic force of the spring 39.

Figure 5:
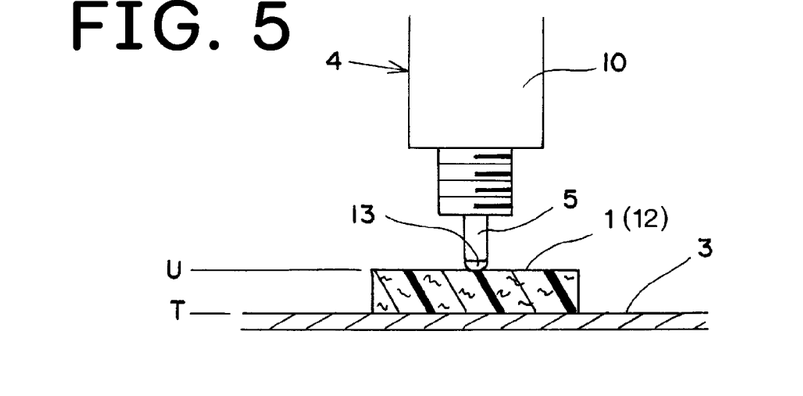
FIG. 5 is a sectional view in a state that the vibrator is contacted to the object-to-be-measured.

Next, from the state of FIG. 17, only the vibrator 5 is lowered from the case 10 to be contacted to the object-to-be-measured 1 (see FIG. 5). After the vibrator 5 is contacted to the object-to-be-measured 1, the vibrator 5 is further lowered by the predetermined distance W against the case 10 by the vertically movable motor 21 (see FIG. 6). Accordingly, the hardness of the object-to-be-measured 1 is measured as pressing the object-to-be-measured 1.

In this manner, since the holder 35 elastically presses the object-to-be-measured 1 to the upper face of the plate 3, the rear face of the object-to-be-measured 1 is intimately contacted to the upper face of the plate 3 so as to improve the measurement accuracy of the thickness and hardness.

The sensor protection cylinder 30 is arranged at the lower part of the case 10. The thread groove 31 is formed on the outer circumferential face of the sensor protection cylinder 30. The sensor protection cover 32 is screwed with the thread groove 31 to be vertically movable against the sensor protection cylinder 30. When the measurement is not performed such as during transportation, the sensor protection cover 32 is contacted to the upper face of the plate 3 prior to the lower end of the vibrator 5 so as to prevent breakage of the vibrator 5 (see FIG. 12). By the way, since the vibrator 5 is only required to be lowered and contacted to the object-to-be-measured 1, it is also possible to adopt a configuration that the vibrator 5 and the holder 35 are lowered against the case 10 without lowering the case 10.

The invention claimed is:

1. A measurement method comprising:
    moving a vibrator (5) of a detection unit (4) relatively towards a flat plate surface (3) having a predetermined area on which an object-to-be-measured is resting, wherein the object-to-be-measured comprises a main body and a raised fabric layer disposed on the main body, the raised fabric layer having a different height and a different hardness than the main body;
    moving the vibrator (5) which is vibrating at a particular frequency closer to a surface of the object-to-be-measured (1) which is mounted on the plate (3) until the frequency changes;
    outputting a first surface contact position where the frequency of the vibrator (5) changes as the vibrator (5) makes contact with a top surface of the raised fabric layer;
    moving the vibrator further towards the flat plate surface until the frequency changes a second time as the vibrator makes contact with a top surface of the main body;
    outputting a second surface contact position where the frequency of the vibrator changes the second time as the vibrator makes contact with the top surface of the main body;
    measuring thickness of the raised fabric layer of the object-to-be-measured by performing a discrimination process between the first surface contact position and the second contact position based on the frequency variation of the vibrator at the first and second contact positions;
    measuring a thickness of the main body of the object-to-be-measured (1) by comparing the second surface contact position and a surface position of the flat plate surface (3) as compared with previously-obtained vibration variation information;
    moving the vibrator (5) further toward the flat plate surface (3) for a predetermined distance from the second surface contact position;
    detecting and outputting a pressure of a reaction force created by the object-to-be-measured against the vibrator (5);
    measuring a hardness of the object-to-be-measured by comparing the reaction force pressure with previously-obtained hardness information; and
    setting or changing various conditions including a vertical movement amount of the vibrator (5), moving pressure of the vibrator (5), moving speed of the vibrator (5), and press depth of the object-to-be-measured (1) due to the vibrator (5) in accordance with the object-to-be-measured (1).

2. The measurement method according to claim 1, further comprising:
    subsequently repeating the measurement operations after mounting another object-to-be-measured (1) with which the object-to-be-measured (1) on the surface of the plate (3) is replaced.

3. The measurement method according to claim 1, further comprising:
mounting a reference body (12) formed on the surface of the plate (3), the reference body having a previously predetermined hardness;
moving the vibrating vibrator (5) closer to a surface of the reference body (12) until the frequency of the vibrator (5) is varied;
setting or correcting frequency information of the vibrator (5) by comparing the varied frequency of the vibrator (5) and previously-set vibration information at a time when the vibrator (5) is brought into contact with the reference body (12).

4. The measurement method according to claim 3, further comprising:
moving the vibrator (5) further toward the plate (3) by a predetermined distance from a surface contact position of the reference body (12);
detecting a pressure of reaction force against the vibrator (5); and
setting or correcting a reaction force pressure value of the vibrator (5) by comparing the reaction force pressure and previously-obtained hardness information at the time when the vibrator (5) presses on the reference body (12).

5. The measurement method according to claim 1, further comprising:
lowering a case (10) to which the vibrator (5) is arranged;
contacting a holder (35) arranged at the case (10) to an upper face of the object-to-be-measured (1);
elastically holding the object-to-be-measured (1) from the upper side as lowering the holder (35) further toward the plate (3) from a surface contact position of the object-to-be-measured (1);
subsequently moving the vibrator (5) against the case (10) closer thereto until the frequency of the vibrator (5) is varied; and
measuring the thickness of the object-to-be-measured (1) based on the frequency variation of the vibrator (5); and/or further comprising the steps of:
moving the vibrator (5) further toward the plate (3) from the case (10) by a predetermined distance from the surface contact position of the object-to-be-measured (1);
detecting and outputting a pressure of a reaction force against the vibrator (5); and
measuring the hardness by comparing the reaction force pressure and the previously-obtained hardness information.

6. A measurement device comprising:
a case (10) arranged above a plate (3) having a flat surface with a predetermined area to receive an object-to-be-measured (1), the case (10) including a vibrator (5) which is attached being vertically movable as vibrating against the case (10);
vibration detection means (15) to detect a variation of vibration of the vibrator (5);
pressure detection means (16) to detect a contact pressure and/or a variation of contact pressure between the vibrator (5) and the plate (3) or the object-to-be-measured (1);
a stroke sensor (17) to detect a vertical movement amount of the vibrator (5); and
a control unit operatively connected to said vibration detection means, said pressure detection means, and said stroke sensor, said control unit being programed and configured to:
move the vibrator (5) relatively towards the plate (3) having a predetermined area on which the object-to-be-measured is resting, wherein the object-to-be-measured comprises a main body and a raised fabric layer disposed on the main body, the raised fabric layer having a different height and a different hardness than the main body;
move the vibrator (5) which is vibrating at a particular frequency closer to a surface of the object-to-be-measured (1) which is mounted on the plate (3) until the frequency changes;
output a first surface contact position where the frequency of the vibrator (5) changes as the vibrator (5) makes contact with a to surface of the raised fabric layer;
move the vibrator further towards the plate until the frequency changes a second time as the vibrator makes contact with a to surface of the main body;
output a second surface contact position where the frequency of the vibrator changes the second time as the vibrator makes contact with the top surface of the main body;
measure thickness of the raised fabric layer of the object-to-be-measured by performing a discrimination process between the first surface contact position and the second contact position based on the frequency variation of the vibrator at the first and second contact positions;
measure thickness of the main body of the object-to-be-measured (1) by comparing the second surface contact position and a surface position of the plate as compared with previously-obtained vibration variation information;
move the vibrator (5) further toward the plate for a predetermined distance from the second surface contact position;
detect and outputting a pressure of a reaction force created by the object-to-be-measured against the vibrator (5);
measure hardness of the object-to-be-measured by comparing the reaction force pressure with previously-obtained hardness information; and
set or change various conditions including a vertical movement amount of the vibrator (5), moving pressure of the vibrator (5), moving speed of the vibrator (5), and press depth of the object-to-be-measured (1) due to the vibrator (5) in accordance with the object-to-be-measured (1).

7. The measurement device according to claim 6, wherein a holder (35) which is vertically moved along with the vibrator (5) and which holds the object-to-be-measured (1) from an upper side as retreating upward when being contacted to the object-to-be-measured (1) is arranged at the case (10).

* * * * *